United States Patent
Skett et al.

(10) Patent No.: US 9,587,205 B2
(45) Date of Patent: Mar. 7, 2017

(54) ACTIVATION OF PEROXYGEN BLEACH

(71) Applicant: Warwick International Group Limited, Flintshire (GB)

(72) Inventors: Matthew Brian Skett, Flintshire (GB); Gary Miller, Flintshire (GB)

(73) Assignee: Warwick International Group Limited, Mostryn Holywell, Flintshire (GB)

( * ) Notice: Subject to any disclaimer, the term of this patent is extended or adjusted under 35 U.S.C. 154(b) by 113 days.

(21) Appl. No.: 14/401,937

(22) PCT Filed: May 16, 2013

(86) PCT No.: PCT/GB2013/051258
§ 371 (c)(1),
(2) Date: Nov. 18, 2014

(87) PCT Pub. No.: WO2013/171492
PCT Pub. Date: Nov. 21, 2013

(65) Prior Publication Data
US 2015/0148280 A1 May 28, 2015

(30) Foreign Application Priority Data

May 18, 2012 (GB) .................................. 1208823.3
Aug. 24, 2012 (GB) .................................. 1215144.5

(51) Int. Cl.
| | |
|---|---|
| C11D 3/30 | (2006.01) |
| C11D 3/39 | (2006.01) |
| C11D 3/395 | (2006.01) |
| C11D 3/34 | (2006.01) |
| C11D 3/32 | (2006.01) |
| C11D 1/02 | (2006.01) |

(Continued)

(52) U.S. Cl.
CPC .......... *C11D 3/3955* (2013.01); *C07C 233/36* (2013.01); *C07C 407/00* (2013.01);
(Continued)

(58) Field of Classification Search
CPC .... C11D 1/02; C11D 3/30; C11D 3/32; C11D 3/3409; C11D 3/3902; C11D 3/3915; C11D 3/3917; C11D 3/3942
(Continued)

(56) References Cited

U.S. PATENT DOCUMENTS

| | | |
|---|---|---|
| 2,955,905 A | 11/1960 | Davies et al. |
| 3,539,629 A | 11/1970 | MacKellar et al. |

(Continued)

FOREIGN PATENT DOCUMENTS

| | | |
|---|---|---|
| CA | 1 110 660 | 10/1981 |
| CN | 1 542 000 A | 11/2004 |

(Continued)

OTHER PUBLICATIONS

Davies, Martin et al., "Kinetics of the hydrolysis and perhydrolysis of the tetraacetylethylenediamine, a peroxide bleach activator", *J. Chem Soc*, Perkin Transactions 2, Chemical Society. Letchworth, GB, vol. 10, pp. 1549-1552 (Jan. 1, 1991).

*Primary Examiner* — Gregory R Delcotto
(74) *Attorney, Agent, or Firm* — Antoinette G. Giugliano; AGG Intellectual Property Law

(57) ABSTRACT

A peracid bleaching species is formed in situ in aqueous wash liquor by reaction of a peroxygen bleach precursor, such as perborate or percarbonate, and a bleach activator. The bleach activator is an acetylated ethylene diamine, that comprises at least 25% triacetyl ethylene diamine. The peracid is formed more rapidly even at low temperatures (F2) compared to use of conventional pure tetracetyl ethylene diamine (F1) and better disinfectant properties result.

15 Claims, 3 Drawing Sheets

(51) Int. Cl.
*C07C 233/36* (2006.01)
*C07C 407/00* (2006.01)
*C11D 11/00* (2006.01)

(52) U.S. Cl.
CPC .................. *C11D 1/02* (2013.01); *C11D 3/30* (2013.01); *C11D 3/32* (2013.01); *C11D 3/3409* (2013.01); *C11D 3/3902* (2013.01); *C11D 3/3915* (2013.01); *C11D 3/3917* (2013.01); *C11D 3/3925* (2013.01); *C11D 3/3935* (2013.01); *C11D 3/3945* (2013.01); *C11D 11/0017* (2013.01); *Y02P 20/582* (2015.11)

(58) Field of Classification Search
USPC ........ 510/311, 313, 376, 492, 499, 501, 505
See application file for complete search history.

(56) References Cited

U.S. PATENT DOCUMENTS

| | | |
|---|---|---|
| 3,824,286 A | 7/1974 | Grimmelikhuysen et al. |
| 4,642,197 A | 2/1987 | Kruse et al. |
| 2004/0002616 A1* | 1/2004 | Preto .................... A01N 37/16 562/2 |

FOREIGN PATENT DOCUMENTS

| | | |
|---|---|---|
| EP | 0 238 341 B1 | 10/1991 |
| EP | 0 484 634 A1 | 5/1992 |
| EP | 1 371 643 A2 | 12/2003 |
| GB | 1 378 308 | 12/1974 |
| GB | 1 423 536 | 2/1976 |

* cited by examiner

ACTIVATION OF PEROXYGEN BLEACH

RELATED APPLICATIONS

This application is the U.S. National Phase of International Application No. PCT/GB2013/051258, filed 16 May 2013, published in English, which application claims priority under 35 U.S.C. §119 or 365 to GB Application No. 1208823.3, filed 18 May 2012 and GB Application No. 1215144.5, filed 24 Aug. 2012. The entire teachings of the above applications are incorporated herein by reference.

The present invention relates to a process in which a peracetic acid is formed by reaction of a peroxygen bleach precursor and a bleach activator which is an acetylating agent, specifically wherein the activator comprises an N-acetylated ethylene diamine material. The material comprises a high proportion of N,N,N'-triacetylethylene diamine and has beneficial effects at low temperatures.

Tetra-acetylethylene diamine (TAED) is a well known activator for peroxide-based bleaches, for instance used in laundry detergents. The peroxide is formed from a persalt such as a perborate, a percarbonate or a persulphate, which can be formulated as a solid material in a detergent composition. The persalt dissolves in the water and decomposes to form a hydroperoxyl ion, which reacts with the activator to give peracetic acid. Peracetic acid is known to be an efficient bleach, in particular for textiles, and has good low temperature efficacy.

TAED has, at each end of the molecule, a nitrogen atom having two acetyl substituents. In the formation of peracetic acid one each of these acetyl groups react to form peracetic acid. The by-product, N,N'-diacetylethylene diamine (DAED) is removed with spent wash liquor. Manufacture of TAED for use in detergents has maximised the yield of TAED from the starting amine or diacetylated diamine compounds, so as to maximise the effective acetyl group availability for weight of ingredient in the detergent.

TAED is prepared by reacting DAED with acetic anhydride, distillation of acetic acid by-product and recovery of TAED as a solid after cooling of the reaction mixture. There have been various descriptions of maximising the yield of TAED by control of the reaction conditions and starting materials, for instance U.S. Pat. No. 3,539,629, CA 1110660 and GB 1378308. It has been suggested to carry out the acetylation reaction, halting this before reaching equilibrium, recovering TAED as a solid and then recycling partially reacted starting materials including N,N,N'-triacetylethylene diamine to be reacted with additional acetic anhydride, in CA 1110660.

In U.S. Pat. No. 3,824,286, polyacetylalkylene diamines are formed by reaction of alkylene diamines with acetic anhydride or ketene. Although it is suggested that triacetylalkylene diamine may be formed, the examples all maximise the level of acetylation and achieve yields of more than 90% of tetra-acetylated compound. In other examples diacetylated diamine is formed from alkylene diamine and acetic anhydride.

Although the objective of using bleach activators is to reduce the temperature at which active bleaching species are formed, TAED is insufficiently soluble in water at room temperature or under conditions of rapid washing, which is increasingly recommended, such that the activation reaction is incomplete during the wash cycle. This results in the activator being wasted. Although attempts have been made to improve the solubility of TAED, for instance by controlling the size of crystals recovered from the acetylation reaction, for instance in EP 0484634, the rate of formation of peracetic acid is still inadequate at low wash temperatures such as 40° C. or lower, and during short washes.

The present inventors have discovered that faster generation of peracetic acid can be achieved where the activator that is used comprises a high proportion of triacetylethylene diamine.

A new process according to the invention provides a process for producing a peracetic acid solution comprising reacting in aqueous solution hydrogen peroxide or a precursor thereof and an N-acetylated ethylene diamine material, and is characterised in that the N-acetylated ethylene diamine material comprises at least 25% by weight N,N,N'-triacetylethylene diamine.

By using N-acetylated ethylene diamine material comprising a high proportion of TriAED, the invention provides rapid generation of peracetic species, even at low wash temperature, thereby allowing peracetic acid activity to take place quickly. The inventors believe this rapid activation is achieved since TriAED is more water soluble than TAED, and therefore dissolves into the water more rapidly, so that the activation reaction takes place quickly.

The invention is illustrated by determining the rate of peracid release as a proportion of the maximum achievable based on acetyl groups available for reaction with perhydroxyl ion. The peracetic is released in an amount of at least 70%, preferably at least 80%, within two minutes of being added to water even at 20° C. By contrast, TAED releases less than 70% within two minutes at 20° C.

In this specification the method used to measure peracid generation is an iodometric titration carried out as follows: 25 g of a mixture of 85% by weight IEC A*base detergent, 10% sodium percarbonate and 5% activator, accurately weighed, is added to it deionised water at 20° C. in a beaker stirred by overhead stirrer at 75 rpm at t=0. After predetermined times from 2 mins, a 50 ml sample of the solution is added to a mixture of 15 ml glacial acetic acid and 5 ml of a 10% solution of potassium iodide at 0° C. and titrated against 0.05M sodium thiosulphate using a suitable indicator for iodine as quickly as possible. The theoretical amount of peracid released (PAR) is calculated as follows:

$$\frac{\text{Weight of activator} \times \text{moles peracid released}}{M.W. \text{ activator}}$$

for TriAED the moles of peracid released is 1, for TAED it is 2.

The actual amount of peracid released (actual PAR) is calculated from the titre of thiosulphate and its molarity, based on the correlation of 2 moles thiosulphate to 1 mole of peracid. The results reported are of actual PAR/theoretical PAR for each time point.

In the present invention the N-acetylated ethylene diamine material preferably comprises at least 50% by weight TriAED, more preferably at least 70% by weight TriAED. The rest of the N-acetylated ethylene diamine comprises TAED as well as some DAED. Preferably the amount of TAED is no more than 20% by weight, more preferably less than 10% by weight, for instance in the range 1 to 5% by weight. The amount of DAED is preferably less than 20% by weight, more preferably less than 10% by weight of the N-acetylated ethylene diamine material.

The process of the invention is generally part of a laundering process. The hydrogen peroxide or precursor is formed, for instance, by adding to water an organic persalt, preferably a perborate or a percarbonate. Usually the persalt and the N-acetylated ethylene diamine material are added together as part of the same detergent composition, for instance a particulate detergent composition.

The invention is of most benefit where the process is a laundering process. The invention is of utility where the laundering process is a machine wash process or is a hand wash process. It is of particular value where the wash is carried out at relatively low temperatures, for instance temperatures of 50° C. or less, preferably 40° C. or less, most preferably using cold water having a temperature in the range 10 to 25° C., most preferably about 20° C.

The invention is also of benefit for short wash cycles, that is, for cycles where the detergent liquor is contacted with the laundry for a period of less than 30 minutes. Most preferably for a period of 15 minutes or less, for instance 10 minutes or less.

The benefit of the invention can be illustrated by comparing biocidal properties of the composition. This may be tested by a method based on standard test method BS:EN 1276 "Test method and minimum requirements for bactericidal activity of chemical disinfectant and antiseptic products that are used in food, industrial, domestic and institutional areas." The improved hygiene effect of the invention is of particular value for hand laundering processes, carried out in unheated water.

In the process, the N-acetylated ethylene diamine material and peroxygen bleach precursor are present in amounts such that the peroxygen bleach precursor is present in a stoichiometric excess as compared to the activator. The weight ratio of the preferred persalt to the N-acetylated ethylene diamine material is generally in the range 1 to 5.

In a detergent composition, the N-acetylated ethylene diamine material and bleach precursor are separately formulated, that is they are present in separate populations of particles, in order to minimise contact during storage and premature chemical reaction between the chemicals. Each of the particles may be formed by conventional detergent formulation processes, and the particles will normally have sizes of normal particular detergents, for instance having average diameter in the range 200 to 800 micrometers, with less than 10% by weight having particle size higher than 1700 micrometers.

It is preferred that the N-acetylated ethylene diamine material is formulated with a binder, preferably a binder which can be combined with the solid N-acetylated ethylene diamine material in the absence of water, for instance in a compactor or, preferably, in another agglomerating technique such as in an extruder. Preferably the mixer is cooled during mixing to keep the temperature below about 90° C. for instance in this range 20-75° C. A suitable binder may have a melting point in the range 30 to 100° C. preferably in the range 40 to 90° C. Suitable examples of binders are polyethyleneglycol, for instance having molecular weight in the range 200 to 100,000 D preferably in the range 1,000 to 20,000 D, and polyethoxylated $C_8$-$C_{24}$ alcohol, such as tallowalcoholethoxylate, and other non-ionic surfactants.

The amount of binder in the N-acetylated ethylene diamine particles is in the range 10 to 20% by weight of the total weight of the particles.

The N-acetylated ethylene diamine particles may additionally comprise other detergent components capable of being formulated in a similar manner, such as lubricant, pigments and/or dyes for colouring the particles and/or sequestrants, for instance sequestrants for heavy metals, which may provide desirable stabilisation of the peracetic acid formed in the reaction process. Such other components are preferably present in amount less than 10%, more preferably less than 5% by weight in the particles. It is often useful to include a lubricant in an extruder mixer for instance a hydrophilic liquid such as a glycol, glycerol or low molecular weight PEG (eg PEG 200-800) or even water or an alcohol.

The present invention further provides a new particulate detergent composition comprising a peroxygen bleach precursor particles and N-acetylated ethylene diamine material particles, and is characterised in that the said N-acetylated ethylene diamine material particles comprise at least 25% by weight TriAED.

The composition may, in addition to the characteristic N-acetylated ethylene diamine material in particulate form, comprise another population of particles containing bleach activator, for instance TAED, in conventional form. Preferably, such activator particles may provide release of peracid at a later time and/or over an extended period for particular end applications e.g. where hygiene is of primary concern, or for longer wash cycles.

The particulate detergent composition of the present invention may further comprise a hydrophobic bleach activator. Certain hydrophobic activators have a hydrocarbon side chain which enables the detergent to target oily stains. A wide range of oily stains may be targeted by altering the length of the hydrocarbon side chain. Such hydrophobic bleach activators may include nonanoyloxybenzene sulfonate (NOBS) and dodecanoyloxybenzene sulfonate (DOBS,) and salts thereof, such as sodium or potassium salts. Preferably, the characteristic N-acetylated ethylene diamine material, may be formulated with a hydrophobic bleach activator. The composition may, in addition to the characteristic N-acetylated ethylene diamine material in particulate form and hydrophobic bleach activator, comprise another population of particles containing bleach activator, for instance TAED, in conventional form. The combination of a hydrophilic bleach activator, such as the N-acetylated ethylene diamine material, and a hydrophobic bleach activator, such as DOBS or NOBS, in a detergent composition of the invention broadens the range of stain removal that the detergent may achieve. For example, TriAED works particularly well against tea, coffee and red wine stains whereas NOBS and DOBS work particularly well against oily stains owing to the hydrophobic nature of the carbon side chain of the NOBS and DOBS bleach activator being attracted to the hydrophobic oil in the stain. Thus, the particulate detergent composition of the invention may be formulated to have varying ratios of N-acetylated ethylene diamine material and a hydrophobic bleach activator according to the nature of the stains the detergent is designed to treat. The use of N-acetylated ethylene diamine material with DOBS or NOBS is useful for cold water applications such as hand washing at low temperatures.

In one embodiment of the present invention, the characteristic N-acetylated ethylene diamine material is formulated with DOBS. Preferably the ratio of N-acetylated ethylene diamine material:DOBS is from 10-90:90-10 such as 10:90 by weight, 20:80 by weight, 30:70 by weight, 40:60 by weight, 50:50 by weight, 60:40 by weight, 70:30 by weight, 80:20 by weight or 90:10 by weight. More preferably the ratio of N-acetylated ethylene diamine material:DOBS is 50:50 by weight, and more preferably the ratio is 80:20 by weight.

In a further embodiment of the present invention, the characteristic N-acetylated ethylene diamine material is formulated with NOBS. Preferably the ratio of N-acetylated ethylene diamine material:NOBS is from 10-90:90-10 such as 10:90 by weight, 20:80 by weight, 30:70 by weight, 40:60 by weight, 50:50 by weight, 60:40 by weight, 70:30 by weight, 80:20 by weight or 90:10 by weight. More preferably the ratio of N-acetylated ethylene diamine material: NOBS is 50:50 by weight, and more preferably the ratio is 80:20 by weight.

In the context of the ratios above, "by weight" means the total weight of the active agent.

The N-acetylated ethylene diamine material comprising high levels of TriAED is formed in an acetylation process of the type used in the prior art. For instance DAED starting material may be acetylated with acetic anhydride under conditions so as to optimise the yield of TriAED. Reaction conditions and recovery of product, with optional purification of product, may be carried out by routine techniques, involving control of starting material proportions, removal of by-products, temperature, recovery of solid product, recycling of proportion of product mixture, by those skilled in the art. Examples of suitable acetylating processes are given in the above-mentioned prior art, conditions being selected so as to control the proportion of TriAED and avoid senses of high levels of TAED. The proportion of TriAED in the product mixture may be increased also by removal of TAED for use in other end applications.

The TriAED containing an acetylated ethylene diamine material is purified by evaporating the mixture to dryness to remove volatiles (including acetic acid by-product) and then the residue is further evaporated to yield the acetylated ethylene diamine mixture as distillate, with the high boiling point by-products remaining as residue.

The accompanying figures relate to the following:

Figure 1:
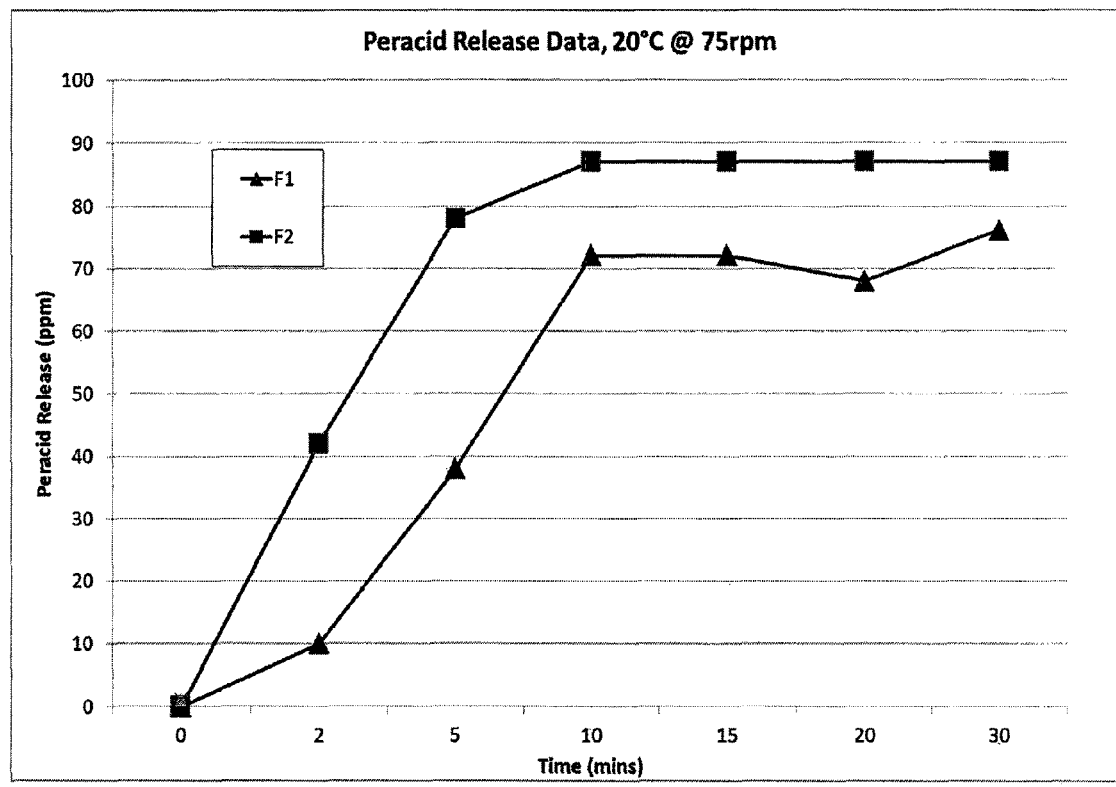
FIGS. 1 and 2 shows the rate of peracid release from an acetylation product mixtures comprising a high proportion of TriAED, as compared to a commercial TAED granule.

The invention is illustrated further by the accompanying examples.

EXAMPLES

Example 1

Ethylene diamine is acetylated to form DAED by reaction with acetic acid. The DAED is further reacted by acetylation using acetyl anhydride. The product mixture is predominately TriAED and TAED with residual amounts of unconverted DAED. TAED is removed from the reaction mixture by cooling, as a solid by filtration. The TriAED enriched reaction mixture is evaporated to dryness to remove volatiles and then the residue is further evaporated to yield an acetylated ethylene diamine mixture as product as distillate with the high boiling point by-products remaining as residue. By controlling the feed composition of the liquor entering this evaporation process, the proportion of TriAED in the acetylated diamine product mixture is controlled.

The feed stream to the plant comprises the following levels of materials

| DAED | <4% |
|---|---|
| TriAED | <20% |
| TAED | <4% |
| Acetic Anhydride | <80% |
| Acetic Acid | <30% |
| Polymeric Amide | <17% |

Composition of product stream from the plant is kept within the range

| DAED | <15% |
|---|---|
| TriAED | <90% |
| TAED | <30% |

Formulation of Acetylated Ethylene Diamine

The product of the plant produced as indicated above was combined with 10% PEG 8000 binder and 1% glycerol as lubricant in an extruder with a cooled mixing zone controlled at a temperature around 43° C. and fed to an extrusion zone controlled at a temperature below 35° C. The batch (300 g) processing time is around 4 minutes. The extruder forms particle sizes having at least 95% in the range 400-1600 µm (by sieve analysis).

Testing of Peracetic Acid Release Rates and Biocidal Testing

Testing of peracetic acid release rate is carried out according to the standard test method described above.

For the biocidal tests, the capability of the activated liquor to kill microorganisms commonly contaminating fabrics and washing machines is determined.

A test method based on BS EN1276 was used to determine the bactericidal efficacy of test solutions against:
*Escherichia coli* ATCC 10536
*Pseudomonas aeruginosa* ATCC 15442
*Staphylococcus aureus* ATCC 6528

Micro-organisms were cultured at 37° C.

The following test formulations were added to 1 liter of sterile 'hard' water, prepared for use in the test method based on BS:EN1276, at 20° C. Test solutions were stirred with an overhead paddle stirrer at 75 rpm at 20° C., F1 and F2 for 5 mins, prior to samples being taken for efficacy testing. The base used was Diao Washing Detergent Base (Nice).

Test formulations F1 and F2 were calculated to deliver a theoretical maximum release of 80 ppm peracetic acid. Tri AED was delivered in the form of an extrudate containing 60.53% Tri AED, 12.99% TAED, residual DAED (7%) with 13% PEG binder, and TAED was delivered as Mykon ATC (trade mark) a commercially available particulate presentation of TAED combining CMC binder and a sequestrant.

0.125 g TAED(8.75%)+0.248 g PCS(17.35%)+
    1.058 g Diao base (73.90%)                                F1

0.25 g Tri AED extrudate*(16.07%)+0.248 g PCS
    (15.94%)+1.058 g Diao base(67.99%)                 F2

*Tri AED extrudate contained—60.53% Tri AED, 12.99% TAED

Bacterial test suspensions were prepared according to the protocol based on the BS EN1276 test protocol. 8 mls of each test solution were inoculated into a mixture of 1 ml bacterial test suspension and 1 ml Bovine Serum Albumin (0.3 g/l BSA for simulated 'clean' conditions) Contact time for test formulations F1 and F2 was 10 mins. Contact temperature was 20° C. After this time 1 ml was taken and added to neutraliser liquid for 5 mins. Samples were diluted down and plated out using Tryptone Soya Agar maintained at 45° C.

Enumeration of bacterial colony forming units and calculation of bacterial log reduction was carried out based on test protocol.

Peracid Release Results

Figure 2:
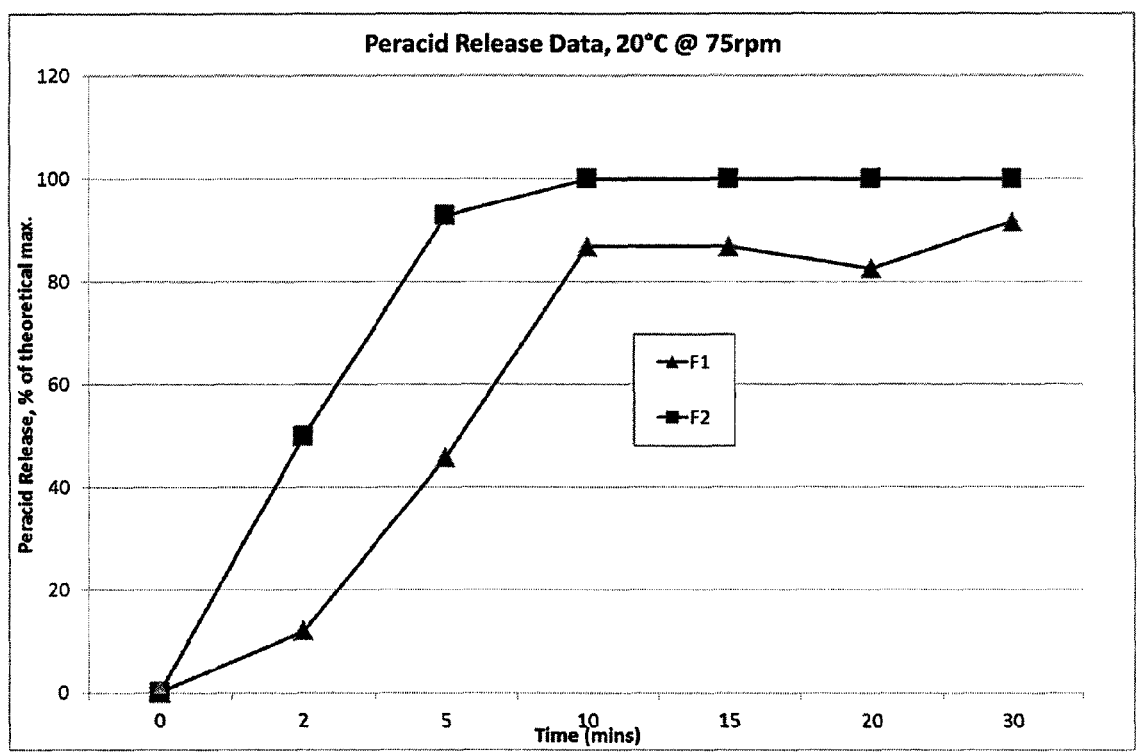

In Table 1 are results obtained for peracid release monitoring of all four of the test formulations. These are also shown graphically in FIG. 1 (ppm PAR) and FIG. 2 (% theoretical max).

TABLE 1

| | | Peracid Release | | |
|---|---|---|---|---|
| Time (mins) | F1 (ppm) | F1 (% th. max) | F2 (ppm) | F2 (% th. max) |
| 0 | 0 | 0 | 0 | 0 |
| 2 | 10 | 12.0 | 42 | 50 |
| 5 | 38 | 45.8 | 78 | 92.8 |
| 10 | 72 | 86.7 | 87 | 100 |
| 15 | 72 | 86.7 | 87 | 100 |
| 20 | 68 | 82.5 | 87 | 100 |
| 30 | 76 | 91.6 | 87 | 100 |

Table 2 shows the results obtained for bactericidal efficacy:

| Test Formulation | Log Reduction E.coli | Log Reduction St. aureus | Log Reduction Ps. aer |
|---|---|---|---|
| F1 | 3.73 | 2.29 | 1.90 |
| F2 | 6.06 | 4.97 | 3.65 |

Figure 3:
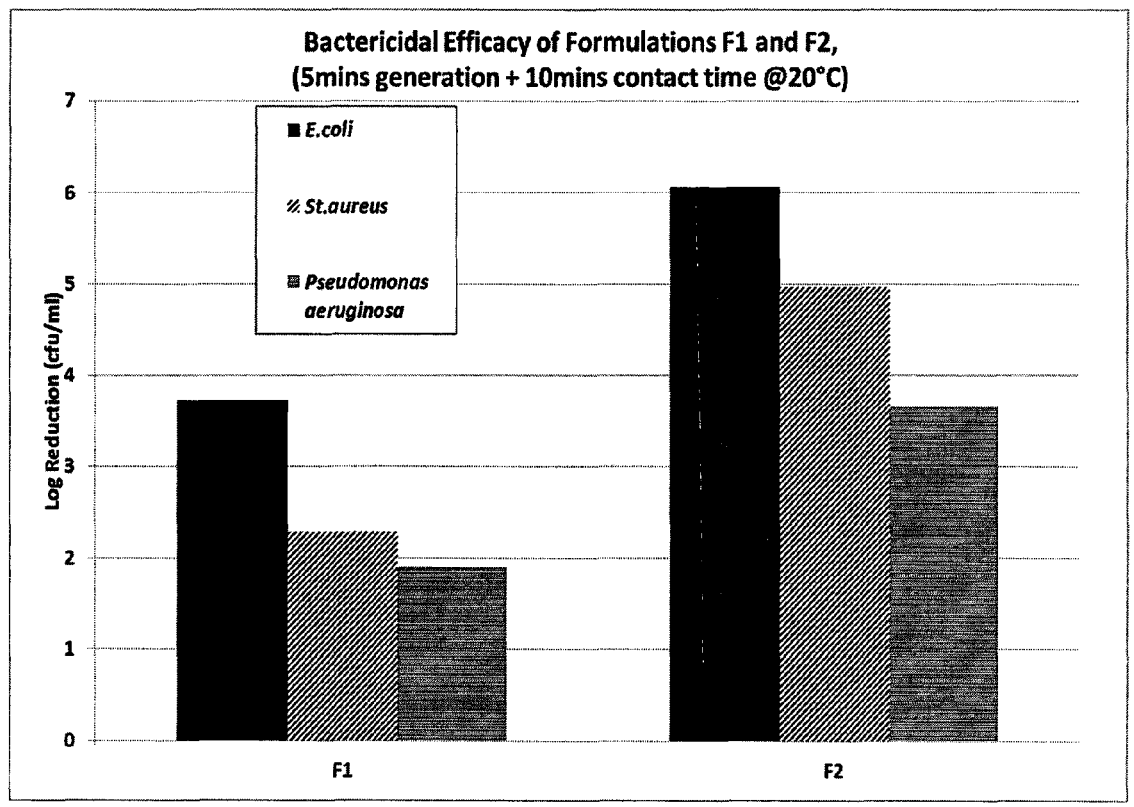
FIG. 3 shows the biocidal efficiency of the solutions.

These are illustrated also in FIG. 3.

CONCLUSION

The aim of the project was to establish the biocidal benefits of using Tri AED, at low temperature and low agitation, conditions indicative of hand wash/soak use, compared to TAED, Tri AED and TAED (Mykon ATC) were included in the test formulations at levels to deliver a theoretical maximum release of 80 ppm and 40 ppm of peracetic acid. This would allow an equal comparison and also show if faster release contributed to the benefits of the activator.

The results show that the Tri AED releases peracetic acid at a much faster rate, at low agitation and temperature, compared to Mykon ATC. Tri AED reaches 92% release in 5 minutes compared to 45% for TAED. Thus the Tri AED test solution demonstrates higher levels of bactericidal activity after 5 mins generation time and 10 mins contact time (F1 and F2).

The results overall do support the use of a Tri AED product to deliver a rapid hygienic effect under low temperature, hand wash/soak conditions.

The invention claimed is:

1. A process for producing a peracetic acid solution comprising reacting in aqueous solution hydrogen peroxide or a precursor thereof and an N-acetylated ethylene diamine material to perhydrolyse the amide bond, characterized in that the N-acetylated ethylene diamine material comprises at least 50% by weight N, N, N'-triacetylethylene diamine (TriAED), at least 5% by weight N,N,N',N'-tetraacetylethylene diamine (TAED) and N,N'-diacetylethylene diamine (DAED), in an amount less than 20% by weight.

2. The process according to claim 1 wherein the N-acetylated ethylene diamine material comprises less than 20% by weight TAED.

3. The process according to claim 1 wherein the N-acetylated ethylene diamine material comprises N,N'-diacetylethylene diamine (DAED), in an amount less than 10% by weight.

4. The process according to claim 1 comprising the preliminary step of providing a solution of the hydrogen peroxide or precursor thereof by adding to water a particulate detergent composition containing an inorganic persalt and the N-acetylated ethylene diamine material.

5. The process according to claim 4 wherein the inorganic persalt and N-acetylated ethylene diamine material are present in the particulate detergent in separate particles.

6. The process according to claim 4 wherein the inorganic persalt is selected from percarbonates and perborates of alkali metals.

7. The process according to claim 4, wherein the particulate detergent composition further comprises surfactant, builder, sequestrant, enzymes, additional bleach activator and/or dyes.

8. The process according to claim 4 wherein the temperature of the water to which the detergent composition is added is no higher than 40° C., and peracetic acid solution is subsequently used to clean a substrate in a cleaning step, followed by a rinsing step in which the spent peracetic acid solution is rinsed from the substrate.

9. The process according to claim 4, wherein the temperature of the water to which the detergent composition is added is no higher than 40° C.

10. A particulate detergent composition comprising peroxygen bleach precursor particles and N-acetylated ethylene diamine material particles, characterized in that the said N-acetylated ethylene diamine material particles comprises at least 50% by weight N,N,N'-triacetylethylene diamine, at least 5% by weight tetra-acetylethylene diamine and N,N'-diacetylethylene diamine in an amount less than 20% by weight.

11. The composition according to claim 10 wherein both sets of particles have average diameters in the range 200-800 µm.

12. The composition according to claim 10 wherein the N-acetylated ethylene diamine material particles are present in an amount in the range 1 to 20% by weight, of the total weight of composition, the peroxygen bleach precursor is present in an amount in the range 2 to 50% by weight, of the total weight of composition, and wherein the weight ratio of peroxygen bleach precursor to acetylated ethylene diamine material in the composition is in the range 1 to 5.

13. The composition according to claim 10 further comprising a hydrophobic bleach activator.

14. The composition according to claim 10 further comprising surfactant, builder, sequestrant, enzymes, additional bleach activator and/or dyes.

15. The composition according to claim 10 wherein the particles containing the N-acetylated ethylene diamine material additionally contain a binder.

* * * * *